(12) United States Patent
Peterson

(10) Patent No.: US 9,095,421 B2
(45) Date of Patent: Aug. 4, 2015

(54) MULTI-LEAFLET COUPLING FOR BRANCH VESSEL CONNECTION

(75) Inventor: Ashley Peterson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 115 days.

(21) Appl. No.: 13/449,785

(22) Filed: Apr. 18, 2012

(65) Prior Publication Data

US 2013/0282102 A1  Oct. 24, 2013

(51) Int. Cl.
*A61F 2/07* (2013.01)
*A61F 2/06* (2013.01)

(52) U.S. Cl.
CPC .............. *A61F 2/07* (2013.01); *A61F 2002/061* (2013.01); *A61F 2002/075* (2013.01)

(58) Field of Classification Search
CPC ..... A61F 2/207; A61F 2002/065; A61F 2/00; A61F 2/91; A61F 2/958; A61F 2210/0076; A61F 2/0063
USPC ........... 623/1.11, 1.25, 1.28–1.29, 1.32, 1.33, 623/1.35, 1.2, 1.16, 1.36
See application file for complete search history.

(56) References Cited

U.S. PATENT DOCUMENTS

| | | | |
|---|---|---|---|
| 3,113,586 A * | 12/1963 | Edmark, Jr. ................ | 137/512.1 |
| 7,306,623 B2 | 12/2007 | Watson | |
| 7,465,316 B2 | 12/2008 | Kujawski | |
| 7,530,997 B2 * | 5/2009 | Roger ........................... | 623/2.38 |
| 7,678,141 B2 | 3/2010 | Greenan et al. | |
| 7,731,741 B2 | 6/2010 | Eidenschink | |
| 2002/0042650 A1 * | 4/2002 | Vardi et al. .................... | 623/1.35 |
| 2002/0188317 A1 * | 12/2002 | Rousseau ....................... | 606/213 |
| 2007/0055356 A1 * | 3/2007 | Eidenschink ................. | 623/1.25 |
| 2007/0067023 A1 * | 3/2007 | Kveen et al. .................. | 623/1.35 |
| 2007/0135904 A1 * | 6/2007 | Eidenschink et al. ........ | 623/1.35 |
| 2008/0046066 A1 * | 2/2008 | Jenson et al. ................. | 623/1.16 |
| 2008/0281395 A1 * | 11/2008 | Eidenschink et al. ........ | 623/1.11 |
| 2010/0268319 A1 | 10/2010 | Bruszewski et al. | |
| 2010/0268327 A1 | 10/2010 | Bruszewski et al. | |

* cited by examiner

*Primary Examiner* — Darwin Erezo
*Assistant Examiner* — Sidharth Kapoor

(57) ABSTRACT

A prosthesis includes a tubular body of a graft material, a plurality of stents coupled to the tubular body, and a coupling. The coupling has a plurality of overlapping leaflets successively coupled to the tubular body around an opening formed in the graft material. The leaflets in a non-deployed configuration lay flush with the graft material of the tubular body and partially cover the opening, and the leaflets in a deployed configuration extend radially outward from the graft material of the tubular body. Delivery and deployment of a branch vessel prosthesis through the opening causes the leaflets to transform from the non-deployed configuration to the deployed configuration, and causes a diameter or width of a passageway defined by the leaflets to increase. Leaflet material properties, as well as size, shape, and sewing patterns on adjacent leaflets may be varied in order to vary the flexibility and/or orientation of the coupling.

20 Claims, 9 Drawing Sheets

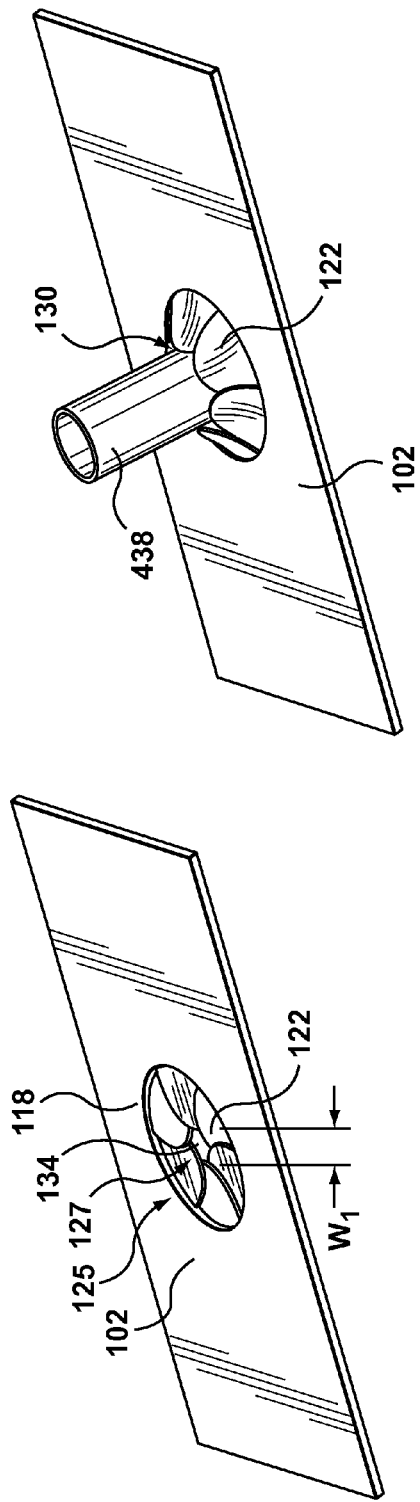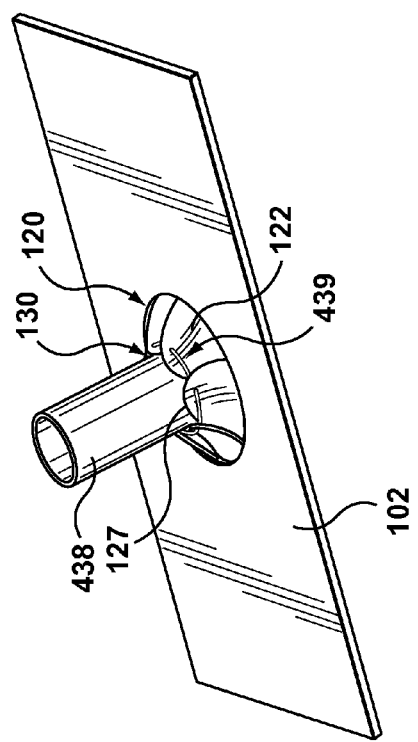

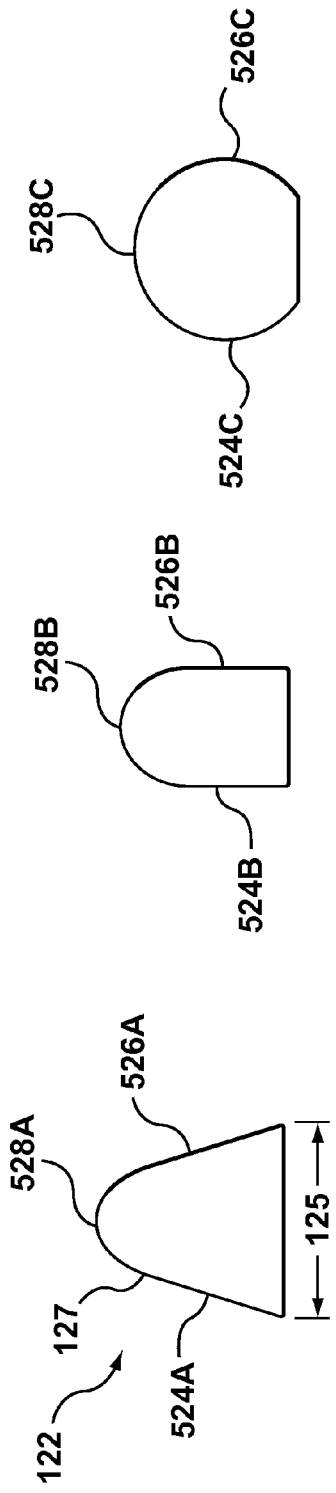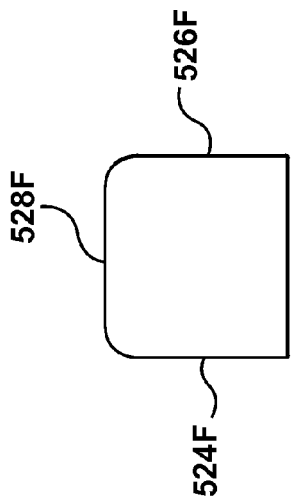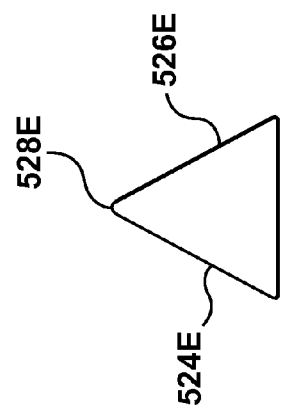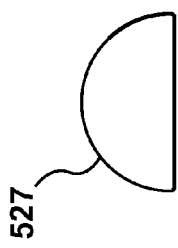

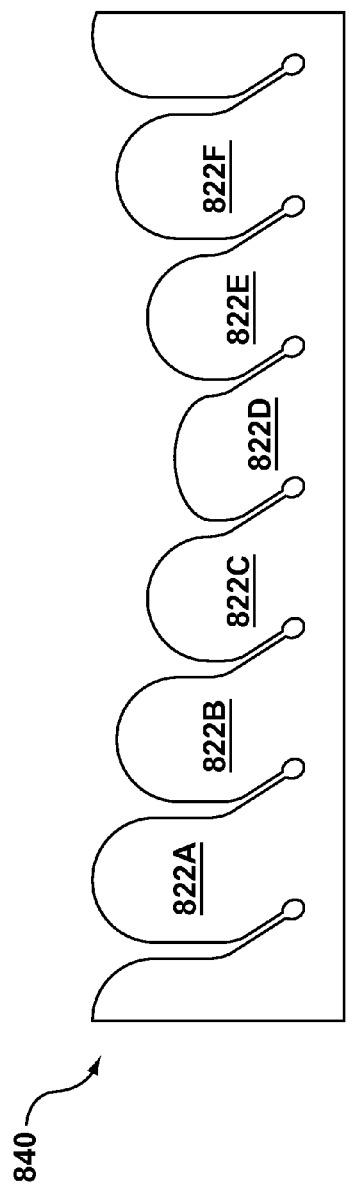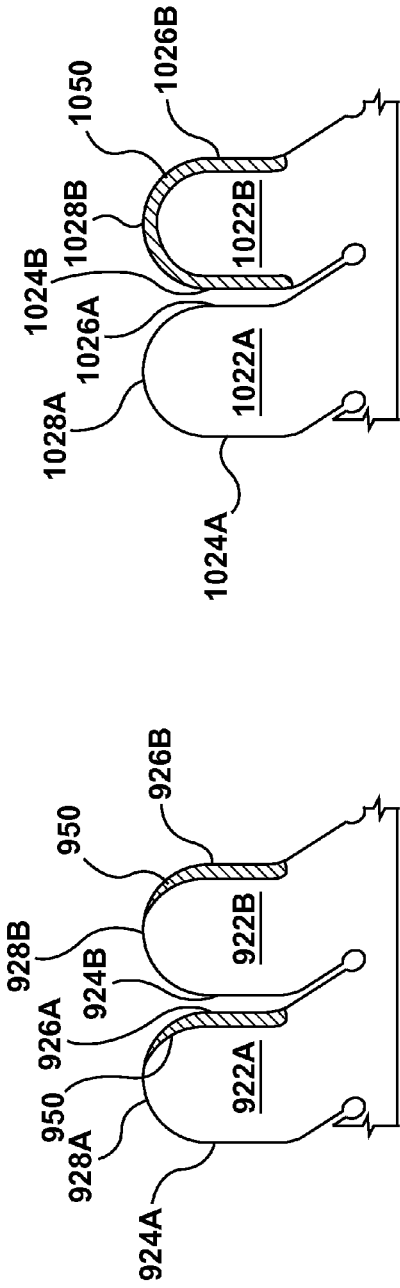

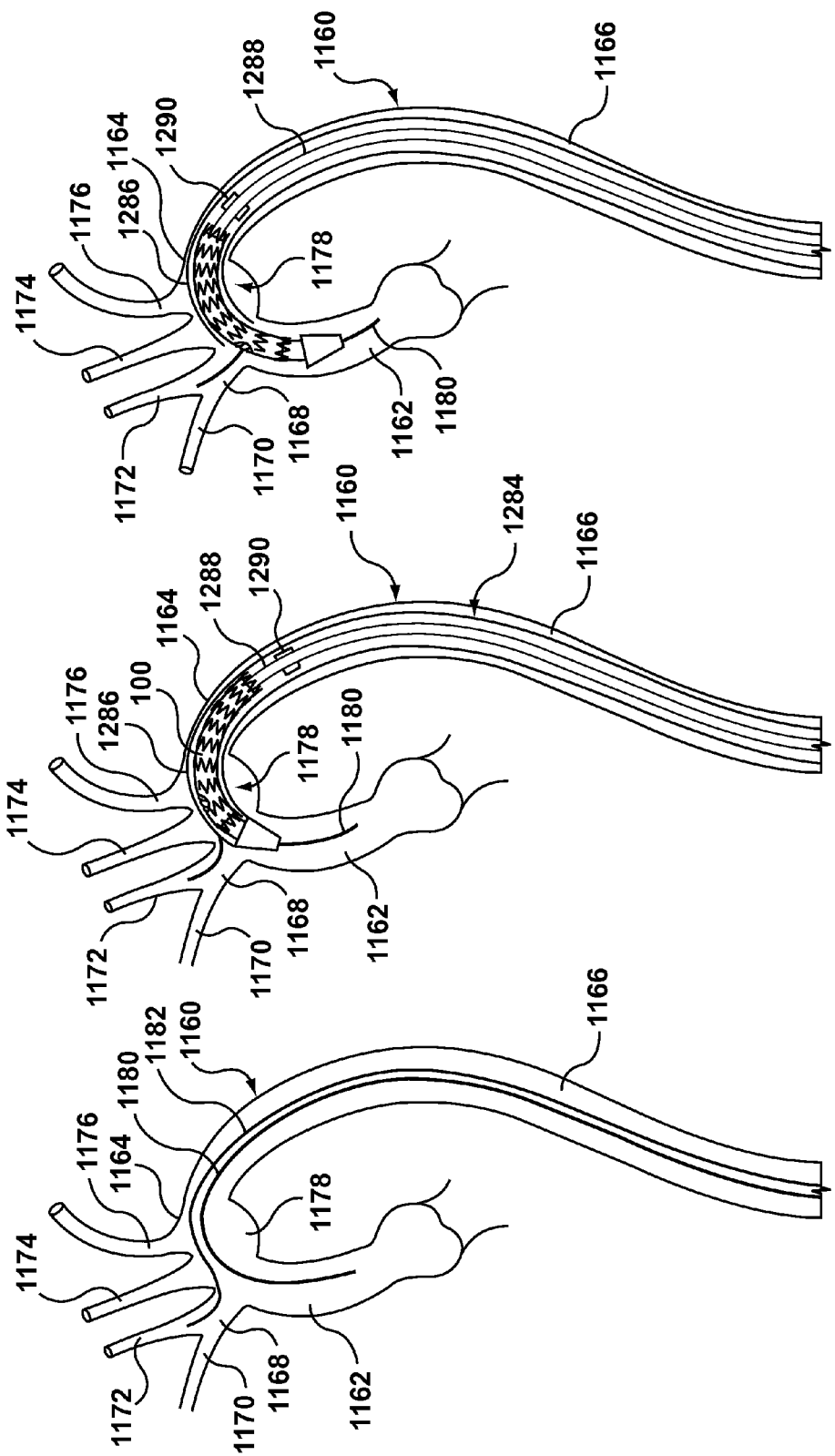

MULTI-LEAFLET COUPLING FOR BRANCH VESSEL CONNECTION

FIELD OF THE INVENTION

This invention relates generally to endoluminal medical devices and procedures, and more particularly to an endoluminal prosthesis or graft having a multi-leaflet coupling for connecting a main graft to a branch vessel graft.

BACKGROUND

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, which could include renal, superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

The thoracic aorta has numerous arterial branches. The arch of the aorta has three major branches extending therefrom, all of which usually arise from the convex upper surface of the arch and ascend through the superior thoracic aperture. The brachiocephalic artery originates anterior to the trachea. The brachiocephalic artery divides into two branches, the right subclavian artery (which supplies blood to the right arm) and the right common carotid artery (which supplies blood to the right side of the head and neck). The left common carotid artery arises from the arch of the aorta just to the left of the origin of the brachiocephalic artery. The left common carotid artery supplies blood to the left side of the head and neck. The third branch arising from the aortic arch, the left subclavian artery, originates behind and just to the left of the origin of the left common carotid artery and supplies blood to the left arm.

For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened and a substitute lumen is sewn across the aneurysmal portion to span it. Such surgery is highly invasive, requires an extended recovery period and, therefore, cannot be performed on individuals in fragile health or with other contraindicative factors.

Alternatively, the aneurysmal region of the aorta can be bypassed by use of an endoluminally delivered tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without challenges. In particular, where a stent-graft is used at a thoracic location, care must be taken so that critical branch arteries are not covered or occluded by the stent-graft, yet the stent-graft must seal against the aorta wall and provide a flow prosthesis for blood to flow past the aneurysmal site. Where the aneurysm is located immediately adjacent to the branch arteries, there is a need to deploy the stent-graft in a location which partially or fully extends across the location of the origin of the branch arteries from the aorta to ensure sealing of the stent-graft to the artery wall.

To accommodate side branches, main vessel stent-grafts having a fenestration or opening in a side wall thereof may be utilized. The main vessel stent graft is positioned to align its fenestration with the ostium of the branch vessel. In use, a proximal end of the stent-graft, having one or more side openings, is prepositioned and securely anchored in place so that its fenestrations or openings are oriented when deployed to avoid blocking or restricting blood flow into the side branches. Fenestrations by themselves do not form a tight seal or include discrete prosthesis(s) through which blood can be channeled into the adjacent side branch artery. As a result, blood leakage is prone to occur into the space between the outer surface of the main aortic stent-graft and the surrounding aortic wall between the edge of the graft material surrounding the fenestrations and the adjacent vessel wall. Similar blood leakage can result from post-implantation migration or movement of the stent-graft causing misalignment between the fenestration(s) and the branch artery(ies), which may also result in impaired flow into the branch artery(ies).

In some cases, the main vessel stent graft is supplemented by another stent-graft, often referred to as a branch stent-graft. The branch graft is deployed through the fenestration into the branch vessel to provide a prosthesis for blood flow into the branch vessel. The branch stent-graft is preferably sealingly connected to the main graft in situ to prevent undesired leakage between it and the main stent-graft. This connection between the branch graft and main graft may be difficult to create effectively in situ and is a site for potential leakage.

In some instances, branch stent-graft extensions are incorporated into the main stent-graft. Such branch graft extensions are folded or collapsed against the main stent-graft for delivery and require complicated procedures, requiring multiple sleeves and guide wires, to direct the branch extension into the branch vessel and subsequently expand. Further, in some instances, such branch stent-grafts tend to return to their folded or collapsed configuration, and thus do not provide an unobstructed flow path to the branch vessel.

Thus, there remains a need in the art for improvements in stent-graft structures for directing flow from a main vessel, such as the aorta, into branch vessels emanating therefrom, such as branch vessels of the aortic arch.

SUMMARY OF THE INVENTION

Embodiments hereof relate to an endovascular prosthesis includes a tubular body of a graft material, the tubular body defining a lumen and having an opening formed therein. A plurality of stents are coupled to the tubular body. A multi-leaflet coupling having a plurality of overlapping leaflets are successively coupled to the tubular body around the opening, the leaflets defining a passageway that is in fluid communication with the lumen of the tubular body. The leaflets in a non-deployed configuration lay flush with the graft material of the tubular body and partially cover the opening of the tubular body and the leaflets in a deployed configuration extend radially outward from the graft material of the tubular body. A diameter or width of the passageway defined by the leaflets increases when the leaflets transform from the non-deployed configuration to the deployed configuration.

Embodiments hereof also relate to a main prosthesis and a branch vessel prosthesis assembly. The main prosthesis is configured for placement in a main vessel, and includes a tubular body of graft material, a plurality of stents coupled to the tubular body, and a multi-leaflet coupling having a plurality of overlapping leaflets successively coupled to the tubular body around an opening formed in the tubular body. The leaflets lay flush with the graft material of the tubular body and partially cover the opening of the tubular body in a non-deployed configuration. The branch vessel prosthesis is configured for placement through the opening formed in the tubular body of the main prosthesis and into a branch vessel that extends from the main vessel. The leaflets in a deployed configuration extend radially outward from the graft material of the tubular body and form a seal onto an outer surface of the branch vessel prosthesis.

Embodiments hereof also relate to a method for excluding an aneurysm at a target location near a junction of a main vessel and a branch vessel. A main prosthesis in a compressed configuration is delivered to the target location in the main vessel and a multi-leaflet coupling is aligned with the branch vessel. The main prosthesis includes a tubular body of graft material, a plurality of stents coupled to the tubular body, and a multi-leaflet coupling having a plurality of overlapping leaflets successively coupled to the tubular body around an opening formed in the tubular body. The leaflets lay flush with the graft material of the tubular body and partially cover the opening of the tubular body. The main prosthesis is then deployed such that the tubular body expands from the compressed configuration to an expanded configuration, wherein the tubular body is disposed in the main vessel. A branch vessel prosthesis in a compressed configuration is delivered through the opening formed in the tubular body of the main prosthesis and into the branch vessel. Delivery of the branch vessel prosthesis through the opening deploys the leaflets to extend radially outward from the graft material of the tubular body and form a seal onto an outer surface of the branch vessel prosthesis.

BRIEF DESCRIPTION OF DRAWINGS

FIG. 2 is a perspective, zoomed-in view of a portion of the stent-graft of FIG. 1.

FIG. 4 is a perspective, zoomed-in view of a portion of the stent-graft of FIG. 3 with a branch vessel prosthesis deployed through the multi-leaflet coupling.

FIG. 4A is a perspective view of a portion of a stent-graft having a multi-leaflet coupling with a branch vessel prosthesis deployed through the multi-leaflet coupling, wherein the multi-leaflet coupling includes a ring around a top of the coupling according to another embodiment hereof.

FIGS. 5A-5F illustrates various configurations of generally U-shaped or V-shaped leaflets according to embodiments hereof.

FIG. 8 illustrates a strip component including a plurality of leaflets for forming a multi-leaflet coupling according to an embodiment hereof, wherein adjacent leaflets differ in size to modify the orientation of the coupling.

FIG. 9 illustrates two adjacent leaflets utilized in forming a multi-leaflet coupling according to an embodiment hereof, wherein side segments of the leaflets include stitching to modify the orientation of the coupling.

FIG. 10 illustrates two adjacent leaflets utilized in forming a multi-leaflet coupling according to an embodiment hereof, wherein one of the leaflets includes stitching to modify the stiffness thereof.

FIGS. 11-16 are schematic illustrations of progressive steps of a method for delivering and deploying the stent-graft of FIG. 1 and a branch stent-graft to a target location.

DETAILED DESCRIPTION

Specific embodiments of the present invention are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis proximal is the portion nearer the heart by way of blood flow path while distal is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as aorta, the invention may also be used in any other blood vessels and body passageways where it is deemed useful. Furthermore, there is no intention to be bound by any expressed or implied theory presented in the preceding technical field, background, brief summary or the following detailed description.

Figure 1:
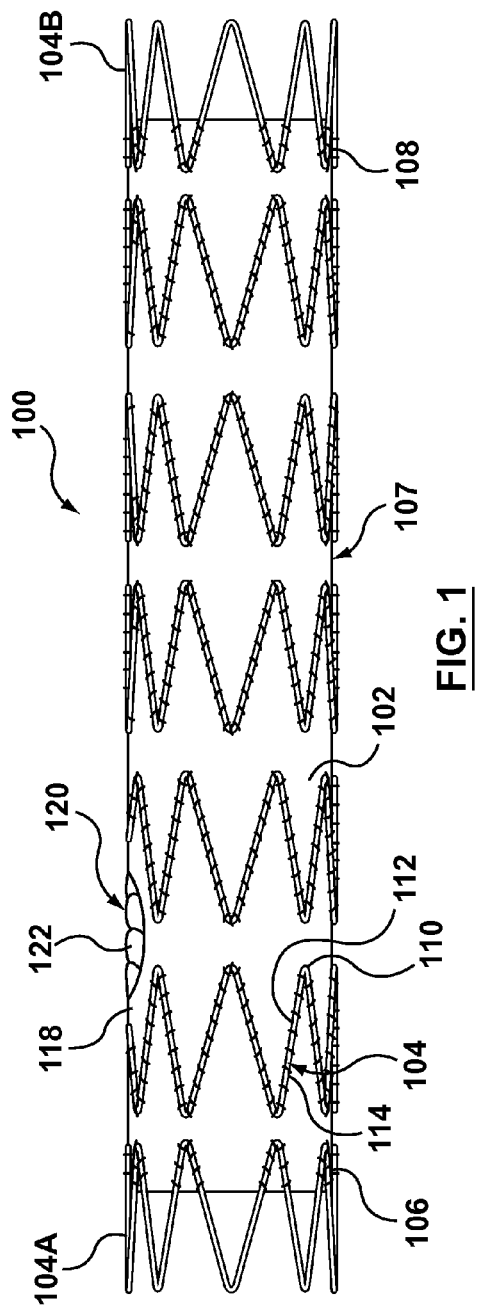
FIG. 1 is a side view of a self-expanding stent-graft having a multi-leaflet coupling according to an embodiment hereof, wherein the multi-leaflet coupling is in a natural or non-deployed configuration.
Figure 3:
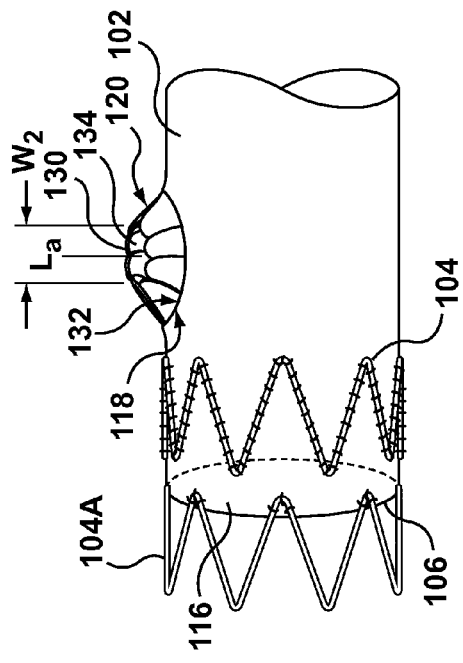
FIG. 3 is a side view of a portion of the stent-graft of FIG. 1, wherein the multi-leaflet coupling is in a deployed configuration.

With reference to FIGS. 1-4, a stent-graft prosthesis 100 is configured for placement in a vessel such as the aorta and includes a multi-leaflet coupling 120 for connecting stent-graft prosthesis 100 to a branch vessel prosthesis 438 (shown in FIG. 4). FIGS. 1-2 illustrate stent-graft prosthesis 100 with coupling 120 in its natural or non-deployed state or configuration and FIGS. 3-4 illustrate stent-graft prosthesis 100 with coupling 120 in its deployed or extended state or configuration, with branch vessel prosthesis 438 omitted from FIG. 3 for illustrative purposes only.

Stent-graft prosthesis 100 includes a tubular graft 102 having a first edge or end 106, a second edge or end 108, and a body 107 there between which defines a lumen 116 through stent-graft prosthesis 100. In an embodiment, first end 106 of graft 102 may be referred to as a proximal end of graft 102 and a proximal end of stent-graft prosthesis 100, and second end 108 of graft 102 may be referred to as a distal end of graft 102 and a distal end of stent-graft prosthesis 100. Graft 102 may be formed from any suitable graft material, for example and not limited to, a low-porosity woven or knit polyester, DACRON material, expanded polytetrafluoroethylene, polyurethane, silicone, ultra high molecular weight polyethylene, or other suitable materials. In another embodiment, the graft material could also be a natural material such as pericardium or another membranous tissue such as intestinal submucosa.

Stent-graft prosthesis 100 also includes at least one radially-compressible stent or scaffold 104 that is coupled to graft 102 for supporting the graft material and is operable to self-expand into apposition with an interior wall of a body vessel (not shown). In the embodiment depicted in FIG. 1, stent-graft prosthesis 100 includes a series of seven independent or separate cylindrical stents 104. Each stent 104 is constructed from a self-expanding or spring material, such as Nitinol, and is a sinusoidal patterned ring including a plurality of crowns or bends 110 and a plurality of struts or straight segments 112 with each crown being formed between a pair of opposing struts. Although shown with seven stents, it will be understood by those of ordinary skill in the art that stent-graft prosthesis 100 may include a greater or smaller number of sinusoidal patterned rings depending upon the desired length of stent-graft prosthesis 100 and/or the intended application thereof. For description purposes only, the stent that is coupled adjacent and proximate to first end 106 of graft 102 is referred to herein as first end stent 104A and the stent that is coupled adjacent and proximate to second end 108 of graft 102 is referred to herein as second end stent 104B but it will be understood by those of ordinary skill in the art that all of the stents may have identical or different patterns or configurations. End stents 104A, 104B may extend outside of or beyond ends 106, 108, respectively, of graft 102 in an open web or free-flow configuration as shown in FIG. 1. In another embodiment hereof (not shown), one or both ends 106, 108 may have a closed web configuration in which the endmost crowns of end stents 104A, 104B are covered or lined by graft 102 and do not extend past or beyond ends 106, 108, respectively, of graft 102. Stents 104 are coupled to graft 102 by stitches or other means known to those of skill in the art. In the embodiment shown in FIG. 2, stents 104 are coupled to an outside surface of graft 102. However, stents 104 may alternatively be coupled to an inside surface of graft 102. When stent-graft prosthesis 100 is used for treating an aneurysm, stents 104 have sufficient radial spring force and flexibility to conformingly engage stent-graft prosthesis 100 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 100, an optimal seal will reduce the chances of aneurysm pressurization and resulting rupture.

Body 107 of tubular graft 102 includes a fenestration or opening 118 formed through a sidewall of the graft. Opening 118 is circular or elliptical, and is longitudinally positioned along body 107 to be aligned with an ostium of a branch vessel when stent-graft prosthesis 100 is deployed in situ. Multi-leaflet connector or coupling 120 is disposed on an outside or inside surface of stent-graft prosthesis 100 corresponding to opening 118 in graft 102. Multi-leaflet coupling 120 includes a plurality of overlapping leaflets or petals 122 that form a conformable yet sealed connection between stent-graft prosthesis 100 and branch vessel prosthesis 438 (see FIG. 4) that is delivered and deployed through opening 118 of stent-graft prosthesis 100. Due to the multi-leaflet design, coupling 120 has the ability to accommodate a wide range of branch vessel prosthesis sizes while still creating a seal onto the branch vessel prosthesis. Blood flow is directed from stent-graft prosthesis 100 and through branch vessel prosthesis 438, and the overlapping leaflets 122 prevent blood flow from leaking around coupling 120 because such leaking may cause undesirable thrombosis and other issues at the coupling.

Referring also to FIG. 5A, each leaflet 122 is a flap of material having a first edge or end 125 that is coupled to graft 102 and a second edge 127 that is not coupled to graft 102. Second unattached edge 127 has a U-shaped or generally U-shaped profile such that the unattached edge 127 of each leaflet 122 has two generally straight side segments 524A, 526A with a top curved segment 528A extending there between. As will be understood by those of ordinary skill in the art, "side" and "top" are relative terms and utilized herein for illustration purposes only. The straight side segments may be slanted or angled away from each other as shown in FIG. 5A in which the two straight slanted side segments 524A, 526A flare apart as they extend from top curved segment 528A, or may be parallel to each other as shown in FIG. 5B in which two straight parallel side segments 524B, 526B extend from a top curved segment 528B. As utilized herein, "generally" U-shaped profiles include: a horseshoe shape as shown in FIG. 5C in which two curved side segments 524C, 526C have ends that converge together as they extend from top curved segment 528C; a semi-circle 527 as shown in FIG. 5D; and an oblong shape as shown in FIG. 5F in which two parallel straight side segments 524F, 526F have a straight top segment 528F there between. In another embodiment hereof, each leaflet may be generally V-shaped as shown in FIG. 5E in which two straight slanted side segments 524E, 526E are connected together by a curved apex 528E. Each leaflet may be considerably longer, shorter, wider, or narrower than shown.

As shown in FIGS. 1-2, in their natural or non-deployed configuration, a plurality of leaflets 122 are successively coupled to graft 102 around opening 118 and lay substantially flush or flat with the graft material of graft 102. As utilized herein, "substantially" flush or flat includes leaflets 122 that are attached to an inner surface or outer surface of the graft material of graft 102 and a longitudinal axis of the leaflets is generally parallel with a surface of the graft material of graft 102. The plurality of leaflets 122 extend into and partially cover opening 118 of graft 102, and the unattached edges 127 of leaflets 122 define an passageway 134 that is in fluid communication with lumen 116 of stent-graft prosthesis 100. In the natural or non-deployed configuration, passageway 134 is a relatively small hole or opening having a diameter or width $W_1$ formed within or on opening 118 of graft 102. Although shown with six leaflets, it will be understood by those of ordinary skill in the art that coupling 120 may include a greater or smaller number of leaflets depending upon the desired diameter or width of coupling 120 and/or the intended application thereof. A portion of each leaflet 122 overlays or overlaps onto an adjacent leaflet 122 such that neighboring unattached edges 127 of the adjacent leaflets are stacked onto one another rather than abutting against each other. In the natural or non-deployed configuration (as compared to the deployed configuration or during the transition from the non-deployed configuration to the deployed configuration), adjacent leaflets 122 have the greatest amount of overlap and the size or width of passageway 134 is the smallest. The amount or degree of overlapping between adjacent leaflets depends on various factors, including the number of leaflets, leaflet shape, fabric material, sealing requirements, and the outer diameter of a branch vessel prosthesis that is to be deployed through passageway 134. In an embodiment, overlap of adjacent leaflets 122 in the natural or non-deployed configuration ranges between 30% and 50%, i.e., 30-50% of a leaflet overlaps onto an adjacent leaflet. A greater degree of overlap accommodates a larger range of branch vessel prosthesis diameters. However, the degree of overlap is limited by the leaflet shape and material, and hence its ability to provide sufficient radial force for sealing, as well as interaction with non-neighboring leaflets and the size of passageway 134.

When a branch vessel prosthesis 438 is delivered through opening 118 of stent-graft prosthesis 100, leaflets 122 of coupling 120 are radially deployed or extended in a direction away from an outer surface of stent-graft prosthesis 100 as shown in FIGS. 3-4. Branch vessel prosthesis 438 is shown as a tubular conduit or component in FIG. 4, but it will be understood by those in the art that the branch vessel prosthesis may be a stent-graft prosthesis such as the one depicted in FIGS. 15-16. Insertion of branch vessel prosthesis 438 through leaflets 122 elevates unattached edges 127 of the leaflets 122 into the ostium of the target branch vessel during deployment to ensure that multi-leaflet coupling 120 everts into the ostium. Insertion of branch vessel prosthesis 438 into coupling 120 transforms the size and shape of passageway 134. More particularly, insertion of branch vessel prosthesis 438 into coupling 120 enlarges the width or diameter of passageway 134 to a width $W_2$, which is greater than width $W_1$ of coupling 120 in a non-deployed or natural configuration. Depending on the size/diameter of branch vessel prosthesis 438, adjacent leaflets 122 move apart or away from each other and the amount of overlap between adjacent leaflets 122 decreases to enlarge or widen passageway 134 to the degree required by the deployed outer diameter of branch vessel prosthesis 438. Thus, when coupling 120 is deployed, width $W_2$ of passageway 134 is variable due to the overlapping nature of the leaflets and depends on the size of branch vessel prosthesis 438. In addition to enlarging/widening passageway 134, insertion of branch vessel prosthesis 438 into coupling 120 elongates or longitudinally extends passageway 134. Leaflets 122 transform from the non-deployed configuration in which they lay substantially flush or flat with the graft material of graft 102 into a deployed configuration in which they form a generally frustoconically shaped component having a base 132 and a top 130. As a result, passageway 134 transforms from the non-deployed configuration in which it is a relatively small hole or opening formed within or on opening 118 of graft 102 into a deployed configuration in which it is an elongated lumen formed or defined by the generally frustoconically shaped component having base 132 and top 130. During deployment, i.e., as it transitions from the non-deployed or natural configuration into the deployed configuration, passageway 134 remains in fluid communication with lumen 116 of stent-graft prosthesis 100. Although multi-leaflet coupling 120 is described as generally frustoconical in shape, base 132 is preferably generally elliptical rather than circular. Base 132 may have, for example and not by way of limitation, a long axis of approximately 20-30 mm and a short axis of approximately 15-20 mm. Further, the height of multi-leaflet coupling 120 may be approximately 10-15 mm. Further, the diameter of the top 130 of multi-leaflet coupling may be approximately 6-9 mm if it is to be used at the junction of the aorta and left common carotid artery or the junction of the aorta and left subclavian artery. If the multi-leaflet coupling 120 is to be used at the junction of the aorta and the brachiocephalic artery, the diameter of the top 130 may be approximately 8-12 mm.

In an embodiment shown in FIG. 4A, a circular band or ring 439 may be disposed around top 130 of multi-leaflet coupling 120. Ring 439 couples or laces unattached edges 127 of leaflets 122 of coupling 120 together and improves or enhances apposition or sealing of top 130 of coupling 120 to branch vessel prosthesis 438. Ring 439 may be a continuous ring or may be a non-continuous ring. Ring 439 may be formed from a solid or hollow tubular ring or wire having a circular or non-circular cross-section. Ring 439 may be made from a biocompatible resilient or elastic material, such as nickel-titanium alloy (nitinol), thermally treated stainless steel, MP35N spring wire, biocompatible silicone, or polyurethane. In another embodiment, ring 439 be formed from a plastically deformable material.

Leaflets 122 of multi-leaflet coupling 120 may be formed from a fabric material that may be the same or different from the graft material of tubular graft 102. For example, leaflets 122 may be a woven or knit polyester, DACRON material, or other suitable fabric materials. Fabric materials may be selected with a desired weave or density, i.e., a loose or tight weave, in order to impart relative stiffness or flexibility to coupling 120. In an embodiment, strands or fibers of an elastic material such as biocompatible silicone or polyurethane may be woven into the fabric material in an orientation to increase the circumferential elasticity of leaflets 122, thereby providing the leaflets with increased radial force for sealing against branch prosthesis 438. Alternatively, leaflets 122 of multi-leaflet coupling 120 may be formed from an elastomer or rubber material that provides increased radial force as compared to fabric materials for improved sealing of coupling 120 onto a branch vessel prosthesis. For example, leaflets 122 may be formed from a woven material comprised entirely of an elastic base material such as biocompatible silicone or silicone based polyurethane materials as described in "Silicone based polyurethane materials: a promising biocompatible elastomeric formulation for cardiovascular applications," Briganti, E., et. al. In another embodiment, leaflets 122 of multi-leaflet coupling 120 are formed from a fabric material such as polyester and a polymer coating is applied to one or more surfaces of the leaflets in order to increase the stiffness and/or spring properties to coupling 120. The coating may be silicone, polyurethane or another polymer that impart stiffness and/or spring properties to the fabric material.

Figure 6:
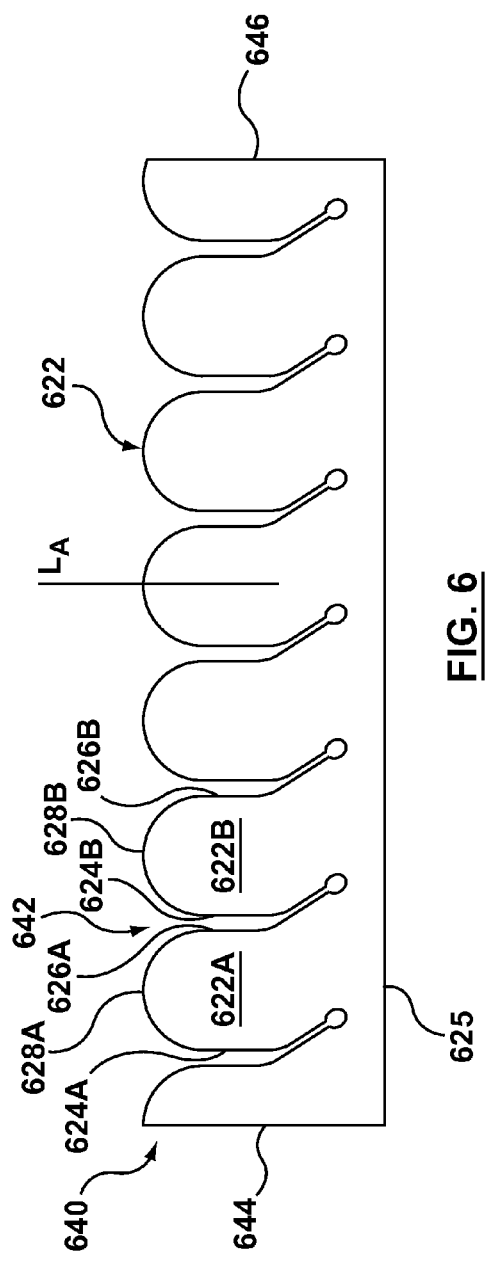
FIG. 6 illustrates a strip component including a plurality of leaflets for forming a multi-leaflet coupling according to an embodiment hereof.

A multi-leaflet coupling according to embodiments hereof may be formed by coupling individual or separate leaflets to graft 102 around opening 118 in an overlapping manner via stitching, adhesive or other suitable method. Alternatively, as shown in FIG. 6, a multi-leaflet coupling according to embodiments hereof may be formed by cutting or shaping a piece of flat material into a strip component 640 having a first end 644, second end 646 and a plurality of consecutive leaflets 622 between ends 644, 646. When cut from a piece of flat material, adjacent leaflets 622A, 622B have a relatively small gap or space 642 there between. Leaflet 622A has two straight side segments 624A, 626A with a top curved segment 628A extending there between, and leaflet 622B of approximately the same size and shape includes two straight side segments 624B, 626B with a top curved segment 628B extending there between. Space 642 is formed between side segment 626A of leaflet 622A and side segment 624B of leaflet 622B. When the coupling is to be attached to stent-graft prosthesis 100, a bottom or longitudinal edge 625 of strip component 640 is coupled to graft 102 around opening 118 via stitching, adhesive, or other suitable method. Longitudinal edge 625 is equal to the circumference of opening 118 so that strip component 640 extends completely around the opening. First end 644 of strip component 640 is then coupled or seamed to second end 646 of strip component 640. Once coupled to graft 102, leaflets 622 in their natural or non-deployed configuration lay flush with the graft material and neighboring side segments of adjacent leaflets 622A, 622B overlap or overlay each other as described with respect to FIGS. 1-2.

Various properties of the leaflets may be tailored or customized to achieve the desired stiffness or flexibility of the coupling. The stiffness or flexibility of the coupling is important because a certain amount of flexibility is required to allow the leaflets to transform from the natural or non-deployed configuration to the deployed configuration, while simultaneously a certain amount of stiffness is required to achieve sealing between the coupling and the expanded branch vessel prosthesis. Coupling 120 is designed to provide a radial force sufficient to seal the coupling and the branch vessel prosthesis, and also to provide resistance to disengagement of the branch vessel prosthesis and the coupling. In an embodiment, coupling 120 is designed to provide an inward radial force in the range of 0.0-1.5 lbf. Depending upon the application, it may be desirable for the coupling to have more flexibility or it may be desirable to increase sealing between the coupling and the expanded branch vessel prosthesis. The stiffness of the leaflets may be modified by material properties described above, including the type of material, the density of a fabric material, and/or the presence of a coating. In addition, the stiffness of the leaflets may be modified by a sewing pattern as will be described in more detail herein with respect to FIGS. 9-10.

In addition, various properties of the leaflets may be tailored or customized to achieve a desired orientation of the coupling relative to the stent-graft prosthesis and opening or fenestration formed therein after the coupling is deployed into the ostium of the branch vessel. In the embodiment of FIGS. 3-4, a longitudinal axis $L_a$ and/or passageway 134 of deployed coupling 120 is shown as forming approximately a ninety degree angle with respect to stent-graft prosthesis 100. As utilized herein with respect to angles, "approximately" includes a range of five degrees greater than or less than stated angle. However, depending upon application as well as individual anatomy, the angle at which a branch vessel extends from a main vessel may vary. The actual angle between the longitudinal axis $L_a$ and/or passageway 134 of deployed coupling 120 and stent-graft prosthesis 100 depends upon the angle at which branch vessel prosthesis 438 is deployed through coupling 120. Coupling 120 is conformable and leaflets 122 adapt to and seal against branch vessel prosthesis 438, therefore rotating or angling the angle of passageway 134 with respect to stent-graft prosthesis 100 as required.

Although coupling 120 is conformable, it may be desirable to initially design and manufacture the coupling to extend from the stent-graft prosthesis such that the longitudinal axis $L_a$ and/or passageway 134 of a deployed coupling extends at an angle other than approximately ninety degrees. The angle or orientation of the coupling may be modified by angling the individual leaflets as described below with respect to FIG. 7 and/or by modifying the shape and/or size of adjacent leaflets as described below with respect to FIG. 8. In addition or in the alternative, the angle or orientation of the coupling may be modified by selectively altering the stiffness of one or more leaflets. As discussed herein, the stiffness of each leaflet may be tailored by modification of material properties including the type of material, density of the weave, and/or presence of a coating, and may be modified by a sewing pattern.

Figure 7:
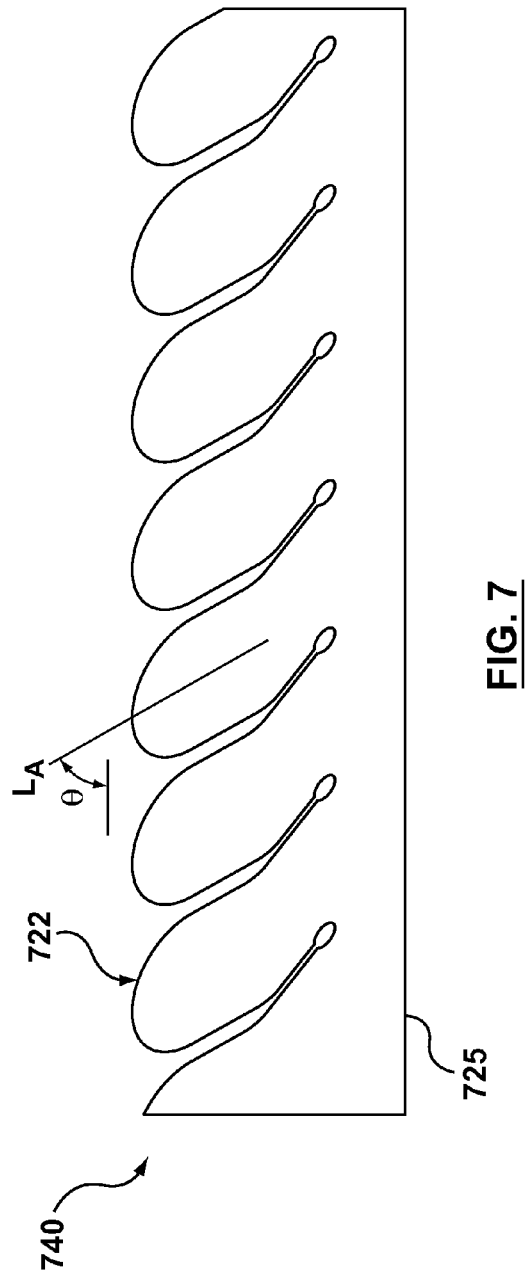
FIG. 7 illustrates a strip component including a plurality of leaflets for forming a multi-leaflet coupling according to an embodiment hereof, wherein the leaflets are angled to modify the orientation of the coupling.
Figure 7A:
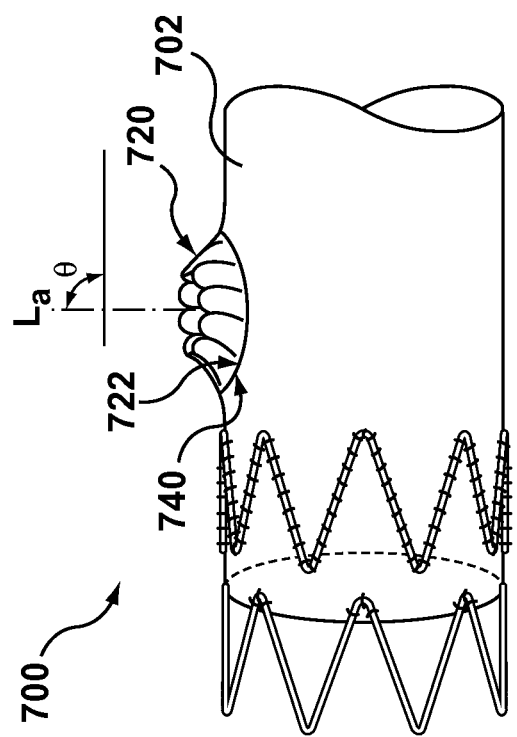
FIG. 7A is a side view of a portion of a self-expanding stent-graft having a multi-leaflet coupling formed from the strip component of FIG. 7, wherein the multi-leaflet coupling is in a deployed configuration and the individually angled leaflets results in an angled coupling with respect to the main graft.

FIG. 7 illustrates an embodiment in which a longitudinal axis $L_A$ of the leaflets of a multi-leaflet coupling are angled with respect to an edge of the strip component. Referring back to FIG. 6, a longitudinal axis $L_A$ of each leaflet 622 is generally perpendicular to edge 625 of strip component 640. When strip component 640 is coupled to graft 102 around opening 118 to form a multi-leaflet coupling, the coupling extends from the stent-graft prosthesis such that the longitudinal axis $L_a$ and/or passageway thereof extends at approximately a ninety degree angle similar to multi-leaflet coupling 120 described with respect to FIGS. 3-4. However, in the embodiment of FIG. 7, each leaflet 722 is angled or offset such that its longitudinal axis $L_A$ forms an angle θ less than ninety degrees with an edge 725 of strip component 740. Depending upon the desired orientation of the coupling when the coupling is deployed in situ, angle θ may vary between ten and eighty-five degrees. FIG. 7A is a side view of a portion of a self-expanding stent-graft 700 having a multi-leaflet coupling 720 formed from strip component 740. Multi-leaflet coupling 720 is in a deployed configuration and the individually angled leaflets 722 result in the longitudinal axis $L_a$ of coupling 720 being angled or offset with respect to graft material 702 of stent-graft 700, i.e., longitudinal axis $L_a$ of coupling 720 forms an angle θ less than ninety degrees with an outer surface of graft material 702 of stent-graft 700. Stated another way, each leaflet 722 is angled such that longitudinal axis $L_a$ of coupling 720 in the deployed configuration is non-perpendicular with respect to an outer surface of graft material 702.

FIG. 8 illustrates an embodiment in which adjacent leaflets of a multi-leaflet coupling are different sizes. A strip component 840 of material includes a plurality of consecutive leaflets 822A, 822B, 822C, 822D, 822E, 822F. Adjacent leaflets incrementally decrease in size between leaflets 822A and leaflet 822D, and then incrementally increase in size between leaflet 822D and leaflet 822F. Different leaflet sizes and/or shapes may vary the orientation or angle of the coupling when the coupling is deployed in situ, thereby accommodating an angled branch vessel. Adjacent leaflets of differing sizes and/or shapes vary the direction/orientation of the coupling because the effective stiffness of the coupling varies around the periphery of the coupling. Regions having less relative stiffness accommodate more angulation between the coupling and a branch vessel prosthesis. In addition to affecting orientation of the coupling, relative sizes, shapes and/or amount of overlap between adjacent leaflets may be tailored to increase the amount of radial force exerted by the coupling onto the branch vessel prosthesis, thereby increasing the degree of sealing if desired.

FIGS. 9-10 illustrate embodiments in which the stiffness and/or orientation of adjacent leaflets may be varied or customized by sewing patterns. More particularly, in the embodiment of FIG. 9, two adjacent leaflets 922A, 922B are shown.

Leaflet 922A has two generally straight side segments 924A, 926A with a top curved segment 928A extending there between, and leaflet 922B of approximately the same size and shape includes two generally straight side segments 924B, 926B with a top curved segment 928B extending there between. Side segments 926A, 926B of each leaflet 922A, 922B include stitching 950 in order to alter the orientation of the multi-leaflet coupling. With identical patterns of partial stitching on each leaflet, the orientation of the multi-leaflet coupling when deployed in situ is shifted or rotated because the portion of each leaflet having stitching 950 thereon is stiffer, i.e., less flexible, than the portion of each leaflet not having any stitching. The degree of rotation depends upon the relative difference in flexibility between side segments 924A, 924B and side segments 926A, 926B, which in turn depends upon properties such as but not limited to the stitching material, stitching density, and the length of the stitched portion.

In the embodiment of FIG. 10, two adjacent leaflets 1022A, 1022B are shown. Leaflet 1022A has two generally straight side segments 1024A, 1026A with a top curved segment 1028A extending there between, and leaflet 1022B of approximately the same size and shape includes two generally straight side segments 1024B, 1026B with a top curved segment 1028B extending there between. Leaflet 1022B includes stitching 1050 around the unattached edge or periphery thereof, i.e., the U-shaped profile formed by side segments 1024B, 1026B and top curved segment 1028B extending there between. As a result, leaflet 1022B is stiffer, i.e., less flexible, than adjacent leaflet 1022A not having any stitching. The orientation of the multi-leaflet coupling when deployed in situ is shifted or rotated because the one or more leaflets have increased stiffness. The degree of rotation depends upon the relative difference in flexibility between adjacent leaflets 1022A, 1022B, which in turn depends upon properties such as but not limited to the stitching material, stitching density, and the length of the stitched portion.

FIGS. 11-16 schematically show a method of delivering stent-graft prosthesis 100 to a target site in a main vessel and a method of delivering a branch stent-graft to a branch vessel. In the example described herein, the stent-graft 100 is delivered and deployed into the aorta 1160. Portions of the aorta 1160 include the ascending aorta 1162, the aortic arch 1164, and the descending aorta 1166. Branching from the aortic arch are the brachiocephalic trunk 1168, the left common carotid artery 1174, and the left subclavian artery 1176. The brachiocephalic trunk branches into the right subclavian artery 1170 and the right common carotid artery 1172. An aneurysm 1178 in the area of the aortic arch 1164 can be difficult to bypass or exclude with a stent-graft because blood flow to the branch arteries must be maintained.

In the embodiment shown in FIGS. 11-16, the aneurysm is sufficiently close to brachiocephalic trunk 1168 that the stent-graft 100 must extend between the brachiocephalic trunk 1168 and the heart. In such a case, multi-leaflet coupling 120 is designed so as to be deployed into the brachiocephalic trunk 1168 to perfuse the brachiocephalic trunk 1168. Prior to the procedure for inserting stent-graft 100, surgical by-pass procedures installing bypass grafts or vessels (not shown) are performed to connect the right common carotid artery 1172 to the left common carotid artery 1174 and the left common carotid artery to the left subclavian artery 1176. Such surgical bypass procedures may be performed one to two weeks prior to insertion of the stent-graft, and present significantly less complications and risk than a surgical solution to repair an aneurysm 1178 in the aortic arch. In this manner, maintaining perfusion to the brachiocephalic trunk 1168, and hence the right common carotid artery 1172, maintains perfusion to the left common carotid artery 1174 and the left subclavian artery 1176. Thus, the openings or ostia to these branch vessels directly from the aortic arch may be blocked by stent-graft 100. In the alternative, multiple multi-leaflet couplings 120 may be provided on stent-graft 100 for perfusion of the left common carotid artery 1174 and/or the left subclavian artery 1176. Further, if the aneurysm only affects the left common carotid artery 1174 and the left subclavian artery 1176, only one by-pass between the left common carotid artery 1174 and the left subclavian artery needs to be performed, and then a stent-graft with a single multi-leaflet coupling 120 can be utilized to perfuse the left common carotid artery 1174. Alternatively, in such a situation, a stent-graft with two multi-leaflet couplings may be provided, one for each of the branch vessels noted. Accordingly, while the embodiment of stent-graft 100 in the method described below includes a single multi-leaflet coupling 120 and the multi-leaflet coupling is deployed in the brachiocephalic trunk 1168, those skilled in the art would recognize that multiple multi-leaflet couplings can be used and the multi-leaflet coupling(s) may be deployed in other branch arteries.

FIG. 11 shows a first guide wire 1180 advanced through the descending aorta 1166, through the aortic arch 1164, and into the ascending aorta 1162 and a second guide wire 1182 advanced through the descending aorta 1166, through the aortic arch 1164, and into brachiocephalic trunk 1168. Guide wires 100, 1182 are typically inserted into the femoral artery and routed up through the abdominal aorta, and into the thoracic aorta, as is known in the art. Second guide wire 1182 may also be locked at its distal or superaortic end so as to prevent second guide wire 1182 from retracting. Access from the brachiocephalic artery or carotid artery may be used to lock second guide wire 1182 at its distal end, as is known to those of ordinary skill in the art as a through-and-through wire technique.

FIG. 12 shows a stent-graft delivery system 1284, with stent-graft 100 compressed therein, advanced over guide wires 1180, 1182 to the target location in the aortic arch 1164. The location of the stent-graft delivery system 1284 and/or the stent-graft 100 may be verified radiographically and delivery system 1284 and/or stent-graft 100 may include radiopaque markers as known in the art. Delivery system 1284 includes at least an outer delivery sheath 1286 and a catheter shaft 1288. Stent-graft prosthesis 100 is mounted on catheter shaft 1288 and outer delivery sheath 1286 covers and restrains prosthesis 100 in a compressed configuration for delivery thereof. As will be understood by those of ordinary skill in the art, delivery system 1284 may include a stop 1290 that prevents longitudinal movement of stent-graft prosthesis 100 as outer sleeve 1286 is retracted or otherwise removed to release stent-graft 100 and/or a stent capture spindle (not shown) which engages proximal-most crowns of stent-graft prosthesis 100 until retraction of the stent capture spindle releases the proximal-most crowns for final deployment of stent-graft prosthesis 100. In an embodiment, delivery system 1284 is the Captivia Delivery System or is similar to the Captivia Delivery System, manufactured by Medtronic Vascular, Inc. of Santa Rosa, Calif. The stent-graft delivery system 1284 described herein is only an example of a delivery system that can be used to delivery and deploy stent-graft prosthesis 100 and many other delivery systems known to those skilled in the art could be utilized. For example, stent-graft prosthesis 100 could be mounted onto a balloon to be expanded when at the target site. Other stent-graft-delivery systems, for example and not by way of limitation, the delivery systems described in U.S. Published Patent Application Publication Nos. 2008/0114442; 2008/0262590; 2010/

0268319; and 2010/0268327; and U.S. Pat. No. 7,264,632, each of which is incorporated herein by reference in its entirety, may be utilized to deliver and deploy stent-graft prosthesis 100. Only a distal end of delivery system 1284 is shown in the figures.

Figure 14:
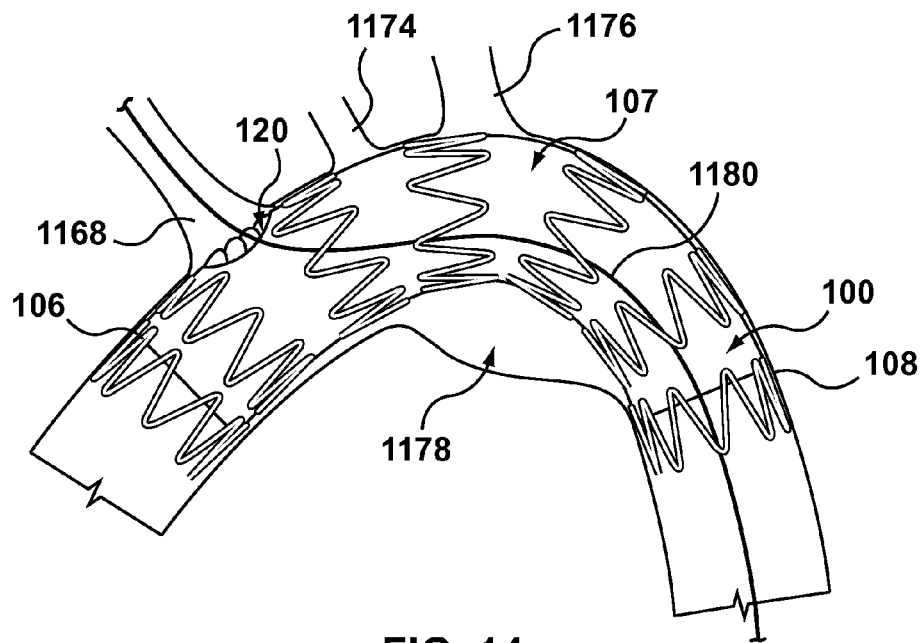

After stent-graft delivery system 1284 is in the location where the multi-leaflet coupling 120 of the stent graft 100 is approximately aligned with the opening into the target branch vessel, outer sleeve 1286 is retracted proximally to begin deployment of stent-graft prosthesis 100, as shown in FIG. 13. Delivery system 1284 may be moved and/or rotated to better align multi-leaflet coupling 120 with the ostium of the branch artery, in this case, the brachiocephalic trunk 1168. After retraction of outer sleeve 1286, multi-leaflet coupling 120 remains in its natural or non-deployed configuration in which the plurality of leaflets 122 lay substantially flush or flat with the graft material of graft 102. Outer sleeve 1286 is further retracted until it no longer restrains any portion of stent graft prosthesis 100, thereby deploying body 107 of the stent graft 100 as shown in FIG. 14. If present, the stent capture spindle (not shown) is then retracted proximally to release proximal-most crowns of stent-graft prosthesis 100 to fully release and deploy the stent-graft 100. Once stent-graft prosthesis 100 is deployed, delivery system 1284 may be removed. Second guide wire 1182 may remain in place in brachiocephalic trunk 1168 or may be replaced by another guide wire.

Figure 15:
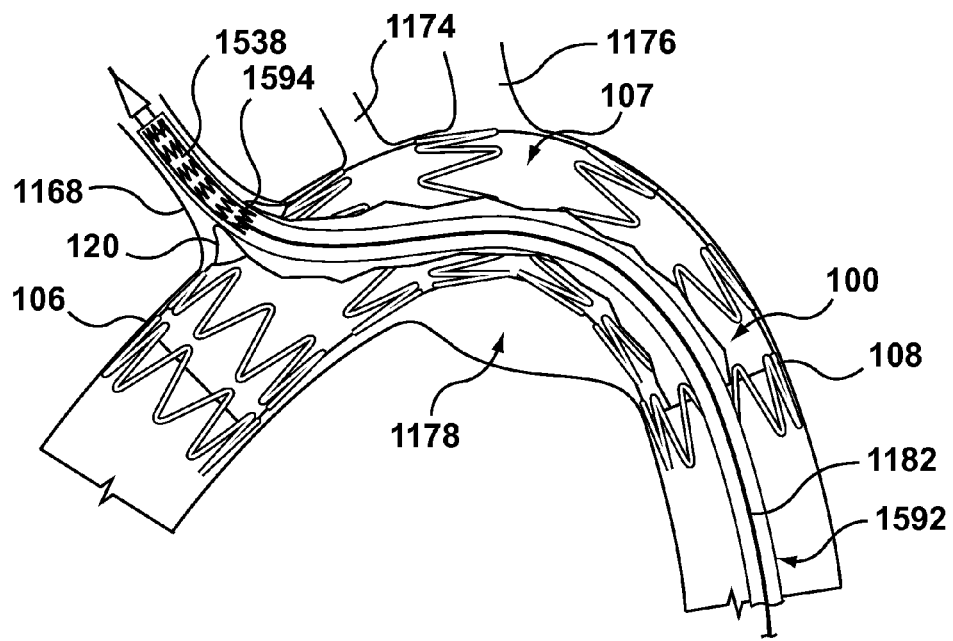

A branch stent-graft delivery system 1592 having a branch stent-graft prosthesis 1538 is then advanced over second guide wire 1182 and into brachiocephalic trunk 1168, as shown in FIG. 15. Branch stent-graft delivery system 1592 may be similar to stent-graft delivery system 1284 described above. Branch stent-graft delivery system 1592 is advanced through multi-leaflet coupling 120 and into the target branch vessel, which in this case is brachiocephalic trunk 1168. Delivery of branch stent-graft delivery system 1592 through multi-leaflet coupling 120 radially deploys or extends leaflets 122 of coupling 120 in a direction away from an outer surface of stent-graft prosthesis 100. Insertion of branch vessel prosthesis 1538 enlarges the lumen or passageway (not shown in FIG. 15) of coupling 120 and elevates the unattached edges of leaflets 122 into the ostium of the brachiocephalic trunk 1168 to ensure that multi-leaflet coupling 120 everts into the ostium. In the deployed configuration shown in FIG. 15, the plurality of overlapping leaflets 122 form a generally frusto-conically shaped component that defines the lumen or passageway there through that is in fluid communication with the lumen of stent-graft prosthesis 100. A proximal portion 1594 of branch stent-graft 1538 remains inside of multi-leaflet coupling 120.

Figure 16:
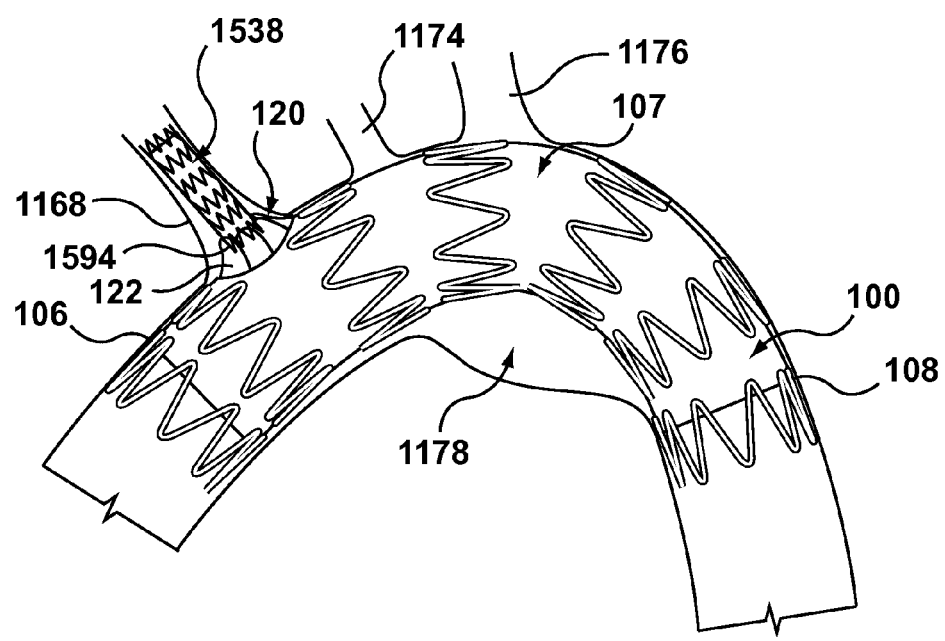

The outer sleeve constraining branch stent-graft 1538 is then retracted proximally, thereby releasing branch stent-graft 1538 from delivery system 1592 so that it may self-expand as shown in FIG. 16. Depending on the size of the expanded branch vessel prosthesis 1538, adjacent leaflets 122 of multi-leaflet coupling 120 move apart or away from each other and the amount of overlap between adjacent leaflets 122 decreases to enlarge the diameter or width of passageway 134 to the degree required by the deployed outer diameter of the expanded branch vessel prosthesis 438. Proximal portion 1594 of branch stent-graft 1538 is disposed within multi-leaflet coupling 120 when branch stent-graft 1538 is expanded, and leaflets 122 of multi-leaflet coupling 120 form a seal onto an outer surface of branch vessel prosthesis 1538. Delivery system 1592 is then withdrawn, leaving stent-graft prosthesis 100 deployed within aortic arch 1164, branch stent-graft 1538 deployed within brachiocephalic trunk 1168, and multi-leaflet coupling 120 forming a flexible yet sealed connection between the main vessel prosthesis and the branch vessel prosthesis.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
a tubular body of a graft material, the tubular body defining a lumen and having an opening formed therein;
a plurality of stents coupled to the tubular body; and
a multi-leaflet coupling having a plurality of overlapping leaflets successively coupled to the tubular body around the opening, the leaflets defining a passageway that is in fluid communication with the lumen of the tubular body, wherein the leaflets in a non-deployed configuration lay flush with the graft material of the tubular body and partially cover the opening of the tubular body and wherein the leaflets in a fully deployed configuration extend radially outward from the graft material of the tubular body, and wherein a diameter of the passageway defined by the leaflets increases when the leaflets transform from the non-deployed configuration to the fully deployed configuration, wherein each of the plurality of leaflets overlaps an adjacent one of the plurality of leaflets in both the non-deployed configuration and the fully deployed configuration.

2. The endovascular prosthesis of claim 1, wherein the amount of overlap between adjacent leaflets decreases when the leaflets transform from the non-deployed configuration to the fully deployed configuration.

3. The endovascular prosthesis of claim 1, wherein each leaflet is a flap of material having a first edge that is coupled to the tubular graft and a second edge that is not coupled to the tubular graft, the second edge having a generally U-shaped profile with two generally straight side segments and a curved segment extending there between.

4. The endovascular prosthesis of claim 1, wherein at least two leaflets of the plurality of leaflets differ in size or shape.

5. The endovascular prosthesis of claim 1, wherein each leaflet is angled such that a longitudinal axis of the coupling in the fully deployed configuration is non-perpendicular with respect to an outer surface of the graft material.

6. The endovascular prosthesis of claim 1, wherein at least a portion of at least one leaflet of the plurality of leaflets is reinforced with stitches.

7. The endovascular prosthesis of claim 1, wherein the leaflets are formed from a fabric.

8. The endovascular prosthesis of claim 7, wherein at least a portion of at least one leaflet of the plurality of leaflets is coated with a polymer.

9. The endovascular prosthesis of claim 1, wherein the leaflets are formed from an elastomer.

10. The endovascular prosthesis of claim 1, wherein each leaflet is a flap of material having a first edge that is coupled to the tubular graft and a second edge that is not coupled to the tubular graft, and a ring is disposed around the second edges of the leaflets.

11. A main prosthesis and a branch vessel prosthesis assembly comprising:
- a main prosthesis configured for placement in a main vessel, the main prosthesis including a tubular body of graft material, a plurality of stents coupled to the tubular body, and a multi-leaflet coupling having a plurality of overlapping leaflets successively coupled to the tubular body around an opening formed in the tubular body, wherein the leaflets lay flush with the graft material of the tubular body and partially cover the opening of the tubular body in a non-deployed configuration; and
- a branch vessel prosthesis configured for placement through the opening formed in the tubular body of the main prosthesis and into a branch vessel that extends from the main vessel, wherein the leaflets in a deployed configuration extend radially outward from the graft material of the tubular body and an inside surface of the leaflets forms a seal onto an outer surface of the branch vessel prosthesis,
- wherein each of the plurality of leaflets overlaps an adjacent one of the plurality of leaflets in both the non-deployed configuration and the fully deployed configuration.

12. The assembly of claim 11, wherein each leaflet is a flap of material having a first edge that is coupled to the tubular graft and a second edge that is not coupled to the tubular graft, the second edge having a generally U-shaped profile with two generally straight side segments and a curved segment extending there between.

13. The assembly of claim 11, wherein at least two leaflets of the plurality of leaflets differ in size or shape or orientation with respect to an outer surface of the graft material when the coupling is deployed.

14. The assembly of claim 11, wherein each leaflet is a flap of material having a first edge that is coupled to the tubular graft and a second edge that is not coupled to the tubular graft, and a ring is disposed around the second edges of the leaflets.

15. A method for excluding an aneurysm at a target location near a junction of a main vessel and a branch vessel, comprising the steps of:
- delivering a main prosthesis in a compressed configuration to the target location in the main vessel, the main prosthesis including a tubular body of graft material, a plurality of stents coupled to the tubular body, and a multi-leaflet coupling having a plurality of overlapping leaflets successively coupled to the tubular body around an opening formed in the tubular body, wherein the leaflets lay flush with the graft material of the tubular body and partially cover the opening of the tubular body and each of the plurality of leaflets overlaps an adjacent one of the plurality of leaflets in the compressed configuration;
- aligning the multi-leaflet coupling with the branch vessel;
- deploying the main prosthesis such that the tubular body expands from the compressed configuration to an expanded configuration, wherein each of the plurality of leaflets overlaps an adjacent one of the plurality of leaflets in the fully expanded configuration, wherein the tubular body is disposed in the main vessel;
- delivering a branch vessel prosthesis in a compressed configuration through the opening formed in the tubular body of the main prosthesis and into the branch vessel, wherein delivery of the branch vessel prosthesis through the opening deploys the leaflets to extend radially outward from the graft material of the tubular body and form a seal onto an outer surface of the branch vessel prosthesis.

16. The method of claim 15, further comprising the steps of:
- deploying the branch vessel prosthesis such that the branch vessel prosthesis radially expands to an expanded configuration and an outside surface of a portion of the branch vessel prosthesis is in contact with an inner surface of a portion of the multi-leaflet coupling, wherein deployment of the branch vessel prosthesis causes a diameter of a passageway defined by the leaflets to increase.

17. The method of claim 15, wherein main vessel is the aortic arch.

18. The method of claim 15, wherein each leaflet is a flap of material having a first edge that is coupled to the tubular graft and a second edge that is not coupled to the tubular graft, the second edge having a generally U-shaped profile with two straight side segments and a curved segment extending there between.

19. The method of claim 15, wherein at least two leaflets of the plurality of leaflets differ in size or shape or orientation with respect to an outer surface of the graft material when the coupling is deployed.

20. The method of claim 15, wherein each leaflet is a flap of material having a first edge that is coupled to the tubular graft and a second edge that is not coupled to the tubular graft, and a ring is disposed around the second edges of the leaflets.

* * * * *